United States Patent
Greve et al.

[11] Patent Number: 5,571,764
[45] Date of Patent: Nov. 5, 1996

[54] ABSORBENT FOR WATER AND AQUEOUS SOLUTIONS

[75] Inventors: Rainer Greve, Bad Segeberg; Gerlinde Ebert, Dreieich/Offenthal; Ulrich Riegel; Fritz Engelhardt, both of Frankfurt, all of Germany

[73] Assignee: Cassella Aktiengesellschaft, Germany

[21] Appl. No.: 590,694

[22] Filed: Jan. 16, 1996

Related U.S. Application Data

[63] Continuation of Ser. No. 123,259, Sep. 20, 1993, abandoned.

[51] Int. Cl.⁶ ............................. B01J 20/26; B01J 20/00; A61M 1/00; A61F 13/15
[52] U.S. Cl. ..................... 502/402; 502/404; 604/317; 604/358
[58] Field of Search ................... 502/402, 404; 604/317, 358

[56] References Cited

U.S. PATENT DOCUMENTS

| 4,851,394 | 7/1989 | Kubodera | 514/54 |
| 5,096,593 | 3/1992 | Wakita et al. | 210/656 |

FOREIGN PATENT DOCUMENTS

| 0273069 | 7/1988 | European Pat. Off. |
| 60-058443 | 4/1985 | Japan . |
| 61-044655 | 5/1986 | Japan . |
| 61-095014 | 5/1986 | Japan . |
| 3-123620 | 5/1991 | Japan . |

*Primary Examiner*—Asok Pal
*Assistant Examiner*—In Suk Bullock
*Attorney, Agent, or Firm*—Connolly & Hutz

[57] ABSTRACT

The present invention relates to absorbents for water and aqueous solutions, in particular for blood, which contain a product from the tuber of a plant from the family of the Araceae.

16 Claims, No Drawings

ABSORBENT FOR WATER AND AQUEOUS SOLUTIONS

This application is a continuation of application Ser. No. 08/123,259 filed on Sep. 20, 1993, now abandoned.

The present invention relates to an absorbent for water and aqueous solutions which contains natural products from the tubers of plants of the family of the Araceae.

Swellable polymers which absorb aqueous solutions are used for the production of napkins, diapers, sanitary towels, tampons and other sanitary articles. The known polymers of this type include crosslinked carboxymethyl cellulose, partially crosslinked polyalkylene oxide, hydrolysates of starch/acrylonitrile graft copolymers and partially crosslinked polyacrylates.

However, there is still a demand for novel swellable substances, in particular those which are distinguished by a capacity for spontaneous absorption and high retention capacity with regard to blood and other serous body fluids as well as by a high absorption capacity for aqueous solutions of substantial electrolyte concentrations.

It is already known that products which belong to the polysaccharides can be obtained from tubers of species from the family of the Araceae. This applies in particular to species of the genus Amorphophallus. From the tubers of the species Amorphophallus Konjak, for example, which can be found mainly in Japan and Indonesia, the so-called Konjak flour can be obtained, and from this the so-called konjakumannan (U.S. Pat. No. 3,928,322). Konjakumannan is a glucomannan which has been known for centuries in Japan as a foodstuff. Glucomannans are gellable products which can be used in particular in the food industry, but also in pharmacy and in other fields.

Surprisingly, it has now been found that the products mentioned are outstandingly suitable as absorbents for water and aqueous solutions, in particular for blood.

The present invention therefore relates to an absorbent for water and aqueous fluids, characterised in that it contains a product from the tuber of a plant from the family of the Araceae.

Examples of suitable plants from the family of the Araceae are the Chinese Taro (Coiocasia esculenta var. antiquorum) and, in particular, species of the genus Amorphophallus, such as A. rivieri, A. aldus, A. bulbifer, A. campanuiatus, A. giganteus, A. variabilis, A. titanum, A. konjak and A. virosus.

Products from Amorphophallus konjak, in particular Konjak flour and Konjakumannan, are particularly preferred.

The claimed product can be obtained from the tubers of the plants in a manner known per se (see, for example, Ullmanns Encyklopädie der technischen Chemie, 3, [Ullmann's Encyclopedia of Industrial Chemistry], 3rd Edition, Volume 13, page 191 (1962), but some of them are also commercially available.

In a preferred embodiment, the absorbents according to the invention contain one or more highly-absorbent, water-swellable synthetic or natural polymers which are swellable in water as further absorbent component. Such polymers are known under the name "superabsorbent polymer" (SAP). They are, in particular, polymers based on (co)polymerised hydrophilic monomers or based on natural hydrophilic polymers.

Particularly suitable natural hydrophilic polymers are, in particular, polysaccharides such as guar, carboxymethylhydroxypropyl guar, starch, cellulose, hydroxyethylcellulose as well as alginates.

Suitable copolymerisable hydrophilic monomers are, in particular, acrylic acid, methacrylic acid, crotonic acid, 2-acrylamido-2-methylpropanesulphonic acid and -phosphonic acid, vinylphosphonic acid, vinylphosphonic semiesters, their salts, acrylamide, N-vinylamides or mixtures of these.

Polymers of the type mentioned are described, for example, in EP-A 316 792, EP-A 343 427, EP-A 391 108, EP-A 400 283, EP-A 417 410, EP-A 421 264 and EP-A 481 370.

Polymers which are preferably employed in the absorbents according to the invention are highly-absorbent, water-swellable synthetic polymers based on (co)polymerised acrylic acid and/or their salts and/or acrylamide.

It is preferred for the highly-absorbent, water-swellable synthetic or natural polymers to have defined particle sizes. Suitable particle sizes are between about 0.1 to about 1 mm, the range between 0.1 and 0.85 mm being preferred and the range between 0.3 to 0.4 mm being particularly preferred.

The ratios by weight between the natural products mentioned and the highly-absorbent, water-swellable synthetic polymers in the mixtures can vary within wide limits. The amount of polymer can vary between 1 and 99% by weight.

Preferred mixtures contain 1 to 20% by weight of natural product and 80 to 99% by weight of polymer.

If appropriate, the absorbents according to the invention can additionally contain adjuvants and additives. Such adjuvants and additives are, for example, binders, polyglycol being particularly suitable. The absorbents according to the invention contain binders in amounts of, preferably, 0 to 30% by weight, particularly preferably in amounts of 0 to 5% by weight.

The absorbents according to the invention absorb water and aqueous solutions in an outstanding manner and can therefore be used in the production of sanitary articles, such as nappies, sanitary towels, tampons and other absorbent products. Their particular advantage is the capacity of spontaneously absorbing blood and other serous body fluids, as well as the retention capacity.

EXAMPLES

Example 1 a) Preparation of a synthetic, absorbent polymer 3650 g of demineralised water are introduced under adiabatic conditions into a 5 l cylindrical wide-mouth reaction flask, 500 g of a freshly boiled starch solution of 50 g maize starch and 450 g of demineralised water, 15 g of a reaction product of 1.98 mol of maleic anhydride and 1.0 mol of polyglycol 300, which also acts as grafting substrate, 1250 g of acrylic acid and 0.625 g of tetraallyloxyethane are dissolved therein, and the mixture is brought to 20° C. Nitrogen is passed into the monomer solution (approx. 2 l/minute) so as to lower the oxygen content. At a content of approx. 0.8 ppm $O_2$, 34 g of a 4% aqueous solution of 2,2'-azobis(amidinopropane) dihydrochloride are added, more $N_2$ is passed in, 17 g of an 0.75% $H_2O_2$ solution are added when the $O_2$ content is approx. 0.08 ppm, and, finally, 4.5 g of an 0.15% ascorbic acid solution are added at an $O_2$ content of approx. 0.01 ppm. Incipient polymerisation, during the course of which the temperature rises to approx. 90° C., results in the formation of a solid gel which is subsequently mechanically comminuted. 1000 g of the comminuted gel are treated with 346 g of 27% sodium hydroxide solution (degree of neutralisation of the acrylic acid =70 mol%), the mixture is kneaded 3 times, and the product is subsequently dried in a thin layer at temperatures above 100° C., ground and, if appropriate, screened.

b) Preparation of an absorbent according to the invention

In a kneader, 1000 g of the neutralised gel of Example 1 are treated with 20 g of commercially available "Amorphophallus konjak radix" powder, and the mixture is kneaded until completely homogeneous and subsequently dried in vacuo at 80° C. in a thin layer, ground and, if appropriate, screened.

Example 2

2.5 kg of screened polymer powder with a particle size of 0.1–0.85 mm, prepared as described in Example 1a, are introduced into a 10 l PETERSON & KELLY mixer. 76.5 g of polyethylene glycol 300, which acts as binder, are sprayed in the course of 5 minutes, and mixing is continued for 1 minute. After 2.5 kg of commercially available "Amorphophallus konjak radix" powder have been added, mixing is continued until the mixture is completely homogenised.

Example 3

In a 500 ml screw-top flask, 50 g of screened polymer powder with a particle size of 0.1–0.85 mm, prepared as described in Example 1a, and 1.8 g of commercially available "Amorphophallus konjak radix" powder are mixed on a roller frame until the mixture is completely homogeneous.

The absorbents according to the invention of the following examples can also be prepared as described in Examples 1b, 2 and 3:

Example 4

Absorbent of 20% by weight of commercially available "Amorphophallus konjak radix" powder and 80% by weight of the polymer as described in Example 1a with a particle size of 0.1–0.85 mm.

Example 5

Absorbent of 98.5% by weight of commercially available "Amorphophallus konjak radix" and 1.5% by weight of polyglycol 300.

Example 6

Absorbent of 3.5% by weight of commercially available "Amorphophallus konjak radix" powder and 96.5% by weight of the polymer as described in Example 1a with a particle size of 0.1–0.4 mm.

Example 7

Absorbent of 1% by weight of commercially available "Amorphophallus konjak radix" powder and 99% by weight of the polymer as described in Example 1a with a particle size of 0.1–0.4mm.

Example 8

Absorbent of 10% by weight of commercially available "Amorphophallus konjak radix" powder, 88.5% by weight of the polymer as described in Example 1a with a particle size of 0.1–0.4 m and 1.5% by weight of polyglycol 300.

Example 9

Absorbent of 20% by weight of commercially available "Amorphophallus konjak radix" powder, 78.5% by weight of the polymer as described in Example 1 with a particle size of 0.1–0.4 mm and 1.5% by weight of polyglycol 300.

Example 10

Absorbent of 90% by weight of commercially available "Amorphophallus konjak radix" powder, 8.5% by weight of the polymer as described in Example 1 with a particle size of 0.1–0.4 mm and 1.5% by weight of polyglycol 300.

Example 11

Absorbent of 1.5% by weight of commercially available "Amorphophallus konjak radix" powder and 98.9% by weight of the polymer as described in Example 1 of Offenlegungsschrift DE 3,738,602 with a particle size of 0.1–0.85 mm.

Example 12

Absorbent of 5% by weight of commercially available "Amorphophallus konjak radix" powder, 93.5% by weight of the polymer as described in Example 1 of Offenlegungsschrift DE 3,738,602 with a particle size of 0.1–0.4 mm and 1.5% by weight of polyglycol 300.

Example 13

Absorbent of 5% by weight of commercially available "Amorphophallus konjak radix" powder and 1.5% by weight of usual commercial starch and 93.5% by weight of the polymer as described in Example 1a with a particle size of 0.1–0.4 mm.

Example 14

Absorbent of 15% by weight of commercially available "Amorphophallus konjak radix" powder and 98.5% by weight of a graft copolymer based on acrylic acid with a degree of neutralisation of 75 mol%.

Example 15

Absorbent of 3% by weight of commercially available "Amorphophallus konjak radix" powder, 1.5% by weight of alginate and 95.5% by weight of the polymer as described in Example 1a with a particle size of 0.1–0.4 mm.

Example 16

Absorbent of 1.5% by weight of commercially available "Amorphophallus konjak radix" powder, 1% by weight of guar flour and 97.5% by weight of the polymer as described in Example 1a with a particle size of 0.1–0.4 mm.

To characterise the absorbents according to the invention, the free absorbency (ATB) and the centrifugal retention (CRET) of the examples of Table 1 below were measured in electrolyte solution. Detailed measurements of the demand absorbency (DA) in blood and electrolyte solution, the penetration of blood, as well as rheological measurements of the products which had been preswollen in blood were furthermore carried out.

The free absorbency and the centrifugal retention are determined with the aid of the teabag method and indicated as the mean of two measurements: approx. 0.2 g of absorbent are sealed in a teabag and immersed for 20 minutes in an electrolyte solution. To determine the absorption, the teabag is now suspended diagonally for 10 minutes and then weighed. To determine the retention, the teabag is first immersed (swelling for 10 minutes) and then centrifuged for 3 minutes in a centrifuge (23 cm diameter, 1400 rpm) and weighed. The blank value is determined with the aid of a teabag without polymer:

$$\text{Absorption/retention} = \frac{\text{end weight} - \text{blank value}}{\text{initial weight}}$$

Demand absorbency: 0.1 g of absorbent are weighed into a Plexiglas cylinder (internal diameter: 25 mm, height: 33 mm, bottom: wire mesh with mesh size 140 µm) and exposed to absorption for 5 minutes. The amount of liquid absorbed is determined via the weight less of the storage container.

In the penetration test, the penetration capacity of sheep's blood into the test substance is assessed visually. A value of 1 means a very good penetration, a value of 6 a poor penetration.

The modulus of elasticity is measured using a controlled-stress rheometer with a plate-plate configuration, manufactured by Carri-Med. To determine the modulus of elasticity, 1 g of absorbent is allowed to swell for 12 hours in 40 g of sheep's blood and the storage modulus of this swollen gel is subsequently measured as a function of the strain at a frequency of 1 Hz. The plateau value is recorded as the modulus of elasticity G'.

The swelling viscosity was determined using a high-shear rotary viscometer. During the measurement, absorbent is sprinkled into stirred sheep's blood at a defined point in time, and the swelling time and the swelling capacity (as a function of time) are recorded.

The readings are compiled in Table 1 below. The abbreviations denote:

ATB—free absorbency

CRET—centrifugal retention

DA—demand absorbency

P—penetration

G'—modulus of elasticity

Q—swelling viscosity

EL 1—0.9% strength sodium chloride solution

EL 2—electrolyte solution composed of 0.9% NaCl, 0.25% $(NH_4)_2HPO_4$, 0.4% $K_2SO_4$, 0.1% $MgCl_2 \cdot 6H_2O$, 0.08% $CaCl_2 \cdot 2H_2O$.

TABLE 1

| | | | Sheep's blood | | | EL 1 | | EL 2 |
|---|---|---|---|---|---|---|---|---|
| | P | G' [Pa] | Q 5'/10'/15' [mPas] | DA [g/g] | DA [g/g] | ATB [g/g] | CRET [g/g] | ATB [g/g] |
| Ex. | | | | | | | | |
| 2 | 2–3 | 989 | 45/51/50 | 9.4 | 32 | 38 | 28 | 28 |
| 3 | 3–4 | 930 | 10/50/145 | 10 | 52.5 | 54 | 38 | 45 |
| 4 | 3 | 1035 | 43/55/48 | 9.5 | 38 | 50 | 36 | 35 |
| 5 | 2 | 100 | 20/20/20 | 8.8 | 15 | 20 | 15 | 18 |
| 6 | 3–4 | 940 | 36/123/150 | 10.2 | 53 | 54 | 38 | 45.5 |
| 7 | 4 | 835 | 81/179/125 | 10.7 | 53.5 | 54 | 37 | 46 |
| 8 | 2 | 855 | 64/88/93 | 10.2 | 41 | 47 | 33 | 40.5 |
| 9 | 2 | 1080 | 77/126/130 | 9 | 35 | 44 | 31 | 36 |
| 10 | 2 | 315 | 46/58/57 | 9 | 20 | 25 | 20 | 22 |
| 11 | 4 | 1060 | 79/170/125 | 10.2 | 52 | 53 | 37 | 45 |
| 12 | 2 | 825 | 58/90/93 | 10 | 43 | 45 | 31 | 40 |
| 13 | 3 | 860 | 42/55/48 | 9.7 | 38 | 51 | 37 | 35 |
| 14 | 4 | 1080 | 81/180/127 | 10.3 | 53 | 54 | 37 | 43 |
| 15 | 3 | 920 | 45/51/50 | 9.4 | 39 | 50 | 35 | 34 |
| 16 | 3 | 970 | 44/55/49 | 9.7 | 38 | 52 | 34 | 36 |
| Comparison: Example | | | | | | | | |
| 1a Particle size: 0.1–0.85 mm | 4–5 | 920 | 8/45/145 | 7.5 | 50 | 53 | 38 | 44 |

We claim:

1. Absorbent for water and aqueous fluids, comprising a natural product from the tuber of a plant from the family of the Araceae and a synthetic polymer based on (co)polymerised hydrophilic monomers.

2. Absorbent according to claim 1, wherein the natural product is from the genus Amorphophallus.

3. Absorbent according to claim 1, wherein the natural product is konjak flour or konjakumannan.

4. Absorbent according to claim 1, wherein the synthetic polymer is based on (co)polymerised acrylic acid, or their salts or acrylamide or a mixture thereof.

5. Absorbent according to claim 1, wherein the content of natural product is 1 to 20% by weight and the content of synthetic polymer is 80 to 99% by weight.

6. Absorbent according to claim 1 further comprises a binder.

7. Absorbent according to claim 6, wherein the binder is polyglycol.

8. A sanitary article comprising the absorbent as claimed in claim 1.

9. The sanitary article according to claim 8, wherein the sanitary article is selected from the group consisting of a napkin, diaper, sanitary towel, and tampon.

10. Absorbent according to claim 1, wherein the araceae are Chinese Taro.

11. Absorbent according to claim 2, wherein said product is selected from the group consisting of *A. rivieri, A. albus, A. bulbifer, A. campanulatus, A. giganteu, A. variabilis, A. titanum, A. konjak* and *A. virosus*.

12. Absorbent according to claim 1, wherein the synthetic polymers have a particle size between about 0.1 to about 1 mm.

13. Absorbent according to claim 1, wherein the synthetic polymers have a particle size between about 0.3 to about 0.4 mm.

14. Absorbent according to claim 1, wherein the synthetic polymers have a particle size between about 0.1 to about 0.4 mm.

15. Absorbent according to claim 6, wherein said binder is in an amount up to 30% by weight.

16. Absorbent according to claim 6, wherein said binder is in an amount up to 5% by weight.

* * * * *